United States Patent
Davis et al.

(10) Patent No.: US 6,730,735 B2
(45) Date of Patent: May 4, 2004

(54) CONJUGATE OF POLYETHYLENE GLYCOL AND CHITOSAN

(75) Inventors: Stanley Stewart Davis, Nottingham (GB); Wu Lin, Nottingham (GB); Fabio Bignotti, Brescia (IT); Paolo Ferruti, Milan (IT)

(73) Assignee: West Pharmaceutical Services Drug Delivery & Clinical Research Centre Limited, Nottingham (GB)

( * ) Notice: Subject to any disclaimer, the term of this patent is extended or adjusted under 35 U.S.C. 154(b) by 0 days.

(21) Appl. No.: 10/350,714

(22) Filed: Jan. 24, 2003

(65) Prior Publication Data

US 2003/0166783 A1 Sep. 4, 2003

Related U.S. Application Data

(62) Division of application No. 09/462,189, filed as application No. PCT/GB98/01971 on Jul. 3, 1998, now abandoned.

(30) Foreign Application Priority Data

Jul. 3, 1997 (GB) ................................ 9713980

(51) Int. Cl.$^7$ ................ C08G 81/00; C08B 37/08; A61K 31/722; A61K 9/27; A61K 9/50
(52) U.S. Cl. ................ 525/54.2; 536/55.2; 514/55
(58) Field of Search ............... 525/54.2; 536/55.2; 514/55

(56) References Cited

U.S. PATENT DOCUMENTS

5,545,423 A 8/1996 Soon-Shiong et al.
5,855,900 A * 1/1999 Nobuhiko ............... 424/425

FOREIGN PATENT DOCUMENTS

| WO | WO 90/09780 A | 9/1990 |
| WO | WO 95/26376 A | 10/1995 |
| WO | WO 97/25067 A | 7/1997 |
| WO | WO 99/01469 A | 1/1999 |

OTHER PUBLICATIONS

Artursson, et al., Pharm. Res., 11, 1358, 1994.
Calvo et al., Chitosan and chitosan/ethylene oxide–propylene oxide block copolymer nanoparticles as novel carriers for proteins and vaccines, Pharmaceutical Research, vol. 14, No. 10, Oct. 1997, pp. 1431–1436.
Hon, Polysaccharides in Medical Applications, Ed. S. Dumitru, Dekker, New York, 1996, pp. 631–649.
Illum et al., Pharm. Res., 11, 1186, 1994.
Mumper et al., Pharm. Res., 13, 701–709, 1996.
Ouchi et al., J. Macromol. Sci. Chem., A28, 959, 1991.
Ouchi, Tatsuro, N–grafted chitosans and preparation and uses in moisturizers, Chemical Abstracts, vol. 113, No. 16, Oct. 15, 1990 [abstract only].
Patel and Amiji, Hydrogels and biodegradable polymers for bioapplications, ACS Symposium Series, 627, p. 209, 1996.
Amiji et al, Polymer Preprints, ACS Division of Polymer Chem., 1994, 35(2), 403.
Peng et al., J. Polymer Science Part A., Polymer Chemistry, 32, 591–596, 1994.
Saito et al., Graft copolymers of poly(ethylene glycol) (PEG) and chitosan, Macromolecular: Rapid Communications, vol. 18, No. 7, Jul. 1997, pp. 547–550.
Takeuchiu et al., Chem. Pharm. Bull., 1994, 42 1954–1956.
Terayama, J. Polymer Science, 8, 243, 1952.
Tomlinson and Rowland, J. Control. Rel., 39, 357–372, 1995.
Zalipsky, Advances in Drug Delivery Research, 16, 157–182, 1995.

* cited by examiner

Primary Examiner—Nathan M. Nutter
(74) Attorney, Agent, or Firm—Akin Gump Strauss Hauer & Feld LLP (57) ABSTRACT

PEG–chitosan conjugates comprising chitosan and polyethylene glycol moieties or derivatives thereof which are bonded together and their use in medicine is described. In one embodiment, the conjugate comprises a chitosan moiety or a derivative thereof and a polyethylene glycol moiety or a derivative thereof which are bonded together via the amino function on the chitosan by the use of an activated chitosan species. In another embodiment, the conjugate comprises a chitosan moiety or a derivative thereof and a polyethylene glycol moiety or a derivative thereof which are bonded together, the chitosan portion of the conjugate having a molecular weight in the range of from 10 kilodaltons to 1000 kilodaltons.

15 Claims, 3 Drawing Sheets

Fig. 1
The flocculation of polystyrene nanoparticles (190nm diameter) by Sodium Sulphate. The effect of Chitosan (CTS) and PEG-Chitosan (PEG-CTS) coatings

CONJUGATE OF POLYETHYLENE GLYCOL AND CHITOSAN

CROSS-REFERENCE TO RELATED APPLICATIONS

This application is a division to U.S. application Ser. No. 09/462,189 filed Sep. 29, 2000, which in turn is an entry under §371 of International Application No. PCT/GB98/01971, filed Jul. 3, 1998 now abn, and published in the English language on Jan. 14, 1999, the contents of each of which are incorporated herein by reference.

BACKGROUND OF THE INVENTION

The present invention concerns a novel conjugate between chitosan and polyethylene glycol (PEG-chitosan conjugate) that may be used in biomedical applications and particularly in the fields of antisense and gene therapy, drug absorption enhancement and targeting using particulate carriers.

Chitosan is a biopolymer material that is derived from chitin. Chemically, chitosan is a polyglucosamine, a linear polymer of β(1→4) linked 2-amino-2-deoxy-D glucopyranose. Chitosan can be derived from chitin through a process of deacetylation. While chitin is insoluble, chitosan in its salt form can demonstrate acceptable solubilities at pHs below 7.0. Chitosan is believed to be non-toxic and can be administered to mucosal surfaces.

Various applications for chitosan have been described in the prior art including its use in wound healing, controlled drug delivery, as a bioadhesive material and to improve the solubility of poorly soluble compounds. More recently, it has been discovered that chitosan, because of its positive charge, can have an effect upon the tight junctions between cells. It has been shown to be effective in improving the paracellular transport of drugs, particularly those that are polar in character. A detailed review of the medical applications of chitosan can be found in the article by Hon in *Polysaccharaides in Medical Applications*, Ed. Dumitru, S., Dekker, New York, 1996, pages 631–649. Specific examples of medical applications for chitosan can also be found in International Application Publication No. PCT/GB90/00291, in Artursson, et al., Pharm. Res. 11, 1358, 1994, and in Illum, et al., Pharm. Res. 11, 1186, 1994.

Chitosan can be obtained in a range of molecular weights from oligomeric materials containing a few units of glucosamine through to higher molecular weight materials of more than 200,000 Daltons. In pharmaceutical applications, the higher molecular weights from 50,000 to 500,000 Daltons are normally preferred. Chitosan can also be obtained in different degrees of deacetylation, but the materials that have a deacetylation of between 60 and 90% are normally preferred. Chitosan can be obtained from various sources, including shellfish, fungi, and other materials. A pharmaceutical grade of chitosan is available from Pronova Limited of Norway.

Because chitosan carries a positive charge, it can be used to interact with negatively charged surfaces as well as with other negatively charged materials including pharmaceuticals. Chitosan can also be used to modify the surfaces of carrier particles. For example, liposomes have been described where chitosan has been bound to their surfaces (Takeuchiu, et al. (1994), Chem. Pharm. Bull. 42, 1954–1956).

Chitosan can be employed in solution, as a powder material, in microspheres, or can be used as a film-forming agent.

It is also known to modify chitosan chemically to produce derivatives with new properties. Examples include N-acylchitosans, N-carboxyalkyl chitosans, N-carboxyacyl chitosans, and O-carboxyalkyl chitosans.

Sample admixtures of chitosan and polyethylene glycol (PEG) are known. For example, chitosan/poly(ethylene oxide) polymer networks have been described by Patel and Amiji (Polymer Preprints, ACS Division of Polymer Chem. 1994, 352, 403 and ACS Symposium Series, 627, Hydrogels and biodegradable polymers for bioapplications, page 209). The hydrogel was prepared by dissolving chitosan in acetic acid to produce a solution. Polyethylene glycol having a molecular weight of 10 kilodaltons (kD) to 1 megadalton (mD) was dissolved in acetic acid and the resulting solution added to the chitosan solution to prepare a physical blend. The blend was then cross-linked with glyoxal to form the gel system. There was no suggestion in the work of Patel and Amiji to bond polyethylene glycol, also known as polyethylene oxide, directly to chitosan to form a PEG-chitosan conjugate.

Chitosan/polymer hydrogels have also been described by Peng, et al. (J. Polymer Science Part A, Polymer Chemistry 32, 591–596, 1994). Here also the chitosan and a polymer (polyoxypropylene glycol) were mixed at acidic pH and then cross-linked with glutaraldehyde.

The attachment of polyethylene glycol to polymeric materials including proteins, carbohydrates, and phospholipids is known—see, for example, the article by Zalipsky, Advances in Drug Delivery Research, 16, 157–182 (1995). This process is often referred to as PEGylation and this term will be used herein. The various chemical procedures have their advantages and disadvantages including the complexity of the method involved, the ability to control the PEGylation of the selected molecule, the reversibility or degradability of the polyethylene glycol polymer linkage, the use of expensive or toxic solvents, etc.

PCT/GB95/00686 describes microspheres for biomedical uses which contain a substantially spherical core particle of a non-water soluble polymer and an outer surface consisting substantially of a water soluble polymer. The water soluble polymer is conjugated to polyethylene glycol and the non-water soluble core particle is attached to the water soluble polymer by the polyethylene glycol (PEG) moiety. The patent application describes detailed examples using PEG-dextran conjugates. Chitosan is also mentioned as a water soluble polymer in the preparation of such microspheres, but no PEG-chitosan conjugates were actually prepared. Moreover, there was no disclosure of particles in which the PEG moieties were pendant and exposed to the external environment.

Ouchi, et al., describes the preparation of PEG-chitosan by acylating the amino groups on the polysaccharide with the monomethyl ether of PEG as the carboxylate and then covalently bonding this compound to 5-fluorouracil (5-Fu) to produce a material for cancer chemotherapy (Ouchi, et al., J. Macromol. Sci. Chem., A28, 959, 1991) ("Ouchi"). The active ester method was used to prepare the PEG-chitosan products in Ouchi and the chitosan was a low molecular weight material having a degree of polymerization of 30 which had been produced by acid treatment of chitosan. The 5-Fu attached to the end of the PEG chain in the PEG-chitosan conjugate and the resulting soluble complex was administered by injection.

Ouchi did not consider that an unmodified PEG-chitosan conjugate could be used for the delivery of anionic macromolecular drugs, such as antisense oligonucleotides and DNA (nucleic acids), nor did they consider that the unmodified conjugate could be used as a coating agent in the field of colloidal drug delivery through the interaction of the positively charged chitosan with negatively charged surfaces and negatively charged colloidal particles. Furthermore, there was no suggestion in Ouchi that such positively charged PEG-chitosan conjugates might be used to provide increased absorption of drugs across mucosal surfaces through their interaction with negatively charged mucus or negatively charged surfaces of epithelial cells.

In the field of gene therapy, it is often important to be able to compact a plasmid material comprising nucleic acids into a small particle for improved administration. The prior art describes how this may be accomplished using cationic polymers such as polylysine as well as cationic lipids (see for example Tomlinson and Rowland, J. Control. Rel. 39, 357–372 (1995), Mumper, et al., Pharm Res. 13, 701–709 (1996)). A patent application PCT/GB97/00022 describes how such compaction can also be achieved using polyamidoamines to which polyethylene glycol has been attached.

However, no examples have been reported where PEG-chitosan was used for the improved compaction of plasmid DNA.

BRIEF SUMMARY OF THE INVENTION

The invention is directed to a composition for the systemic uptake of a drug across a mucosal membrane. The composition includes a polyethylene glycol-chitosan conjugate. The conjugate includes a chitosan or a chitosan derivative moiety and a polyethylene glycol or a polyethylene glycol derivative moiety. The composition is formulated for delivery to a mucosal membrane. In a preferred embodiment, the composition contains a polyethylene glycol-chitosanic conjugate represented by the formula: —[$C_m$—$NR^1{}_2$]$_p$—, wherein $C_m$ is a remainder of a monomeric unit of a chitosan or a chitosan derivative moiety; p is an integer of 50 to 6000; $R^1$ is independently selected from a hydrogen atom and wherein $R^2$ is selected from a bond and a first divalent organic group; X is selected from an oxygen atom, a sulfur atom and the group —$NR^3$—, wherein $R^3$ is selected from a hydrogen atom and a monovalent organic group; and [PEG] is a polyethylene glycol or polyethylene glycol derivative moiety, provided that 1% to 99% of the groups represented by $R^1$ is Also provided is a method for the preparation of a composition for systemic uptake of a drug across a mucosal membrane, where the composition used in the method includes a polyethylene glycol-chitosan conjugate. In the method, one prepares the polyethylene glycol chitosan conjugate by bonding the amino function of an activated chitosan species to a polyethylene glycol or to a polyethylene glycol derivative moiety.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings.

DETAILED DESCRIPTION OF THE INVENTION

We have discovered that the modification of chitosan by the covalent bonding of a polyethylene glycol moiety to the chitosan molecule through the amino function (PEGylation) results in a polymer conjugate material that can display beneficial pharmaceutical properties and provides an opportunity for improvements in the delivery of drugs, vaccines, diagnostic agents as well as for nucleic acids in the field of gene therapy. In particular, the PEG-chitosan conjugate may be interacted with anionic materials, such as antisense oligonucleotides and DNA (nucleic acid), and may be used to enhance drug absorption or for targeting using particulate carriers.

According to a first aspect of the present invention there is provided a polymer conjugate comprising a chitosan moiety or a derivative thereof and a polyethylene glycol (PEG) moiety or a derivative thereof which are bonded together via the amino function on the chitosan by the use of an activated chitosan species.

According to a second aspect of the present invention there is provided a polymer conjugate comprising a chitosan moiety or a derivative thereof and a polyethylene glycol (PEG) moiety or a derivative thereof which are bonded together, the chitosan portion of the conjugate having a molecular weight in the range of from 10 kilodaltons to 1000 kilodaltons.

According to a third aspect of the present invention there is provided a composition comprising a complex formed between a PEG-chitosan conjugate and a therapeutic agent selected from the group consisting of oligonucleotides and nucleic acids. The PEG-chitosan conjugate comprises a chitosan moiety or a derivative thereof and a polyethylene glycol moiety or a derivative thereof which are bonded together.

According to yet another aspect of the present invention there is provided particular compositions comprising a polymer conjugate in the form of chitosan covalently attached to polyethylene glycol that can be used in drug delivery.

Chitosan is a polymeric material comprising repeating monomeric units having the formula:

where p is an integer and represents the number of monomeric units in the chitosan chain, i.e., the degree of polymerization.

In addition to the monomeric units shown above, chitosan will generally contain a proportion of the monomeric units found in chitin. This proportion will depend on the degree of deacetylation. Typically, the degree of deacetylation is in the range of from 99% to 10%, and is preferably in the range of from 90% to 20%, more preferably in the range of from 85% to 40%.

It is possible to vary the degree of conversion of the chitosan to the PEGylated form by controlling the chemical reaction used to form the conjugate and so have a range of PEG-chitosan complexes for different pharmaceutical applications. The polyethylene glycol moiety may well increase the solubility of the PEG-chitosan conjugate or, more importantly, the solubility of a PEG-chitosan conjugate that has been complexed with a therapeutic agent such as a drug or a nucleic acid.

The conversion of the amino (NH2) functions within chitosan to the PEGylated form can be within the range of 1 to 99%. However, it is preferred that the conversion is in the range 10 to 90% and more preferably in the range of 10 to 50%.

When it is desired to use the PEG-chitosan conjugate to interact with a drug or a biological membrane or to modify the tight junction of a mucosal surface or to coat a negatively charged microparticle, then the PEG-chitosan conjugate should have a residual positive charge.

In one embodiment, the PEG-chitosan conjugate should retain sufficient positive charge to allow it to interact with negatively charged (anionic) materials such as oligonucleotides or nucleic acids (DNA) and provide for compaction of the anionic species. By compaction we mean reduction in particle size as measured by a technique such as atomic free microscopy. or photon correlation spectroscopy.

In another embodiment, the PEG-chitosan conjugate should have sufficient positive charge to allow it to interact with negatively charged colloidal carriers intended for drug delivery, such as emulsions, liposomes, microspheres, and microcapsules as well as negatively charged drug particles of a size less than 100 microns.

In yet another embodiment, the PEG-chitosan conjugate should have a sufficient positive charge to interact with mucin or epithelial cells.

A positive charge on the PEG-chitosan conjugate can be evaluated by studying the interaction of the conjugate with a negatively charged polymer so that a polyelectrolyte complex is formed as described by Terayama in J. Polymer Science, 8, 243 (1952). Alternatively, the PEG-chitosan conjugate can be absorbed onto a polymer particle such as a polystyrene microsphere of about 1 micron in size and in the charge on the system evaluated by particle microelectrophoresis using an apparatus such as the Malvern Zeta Sizer. By a sufficient positive charge for interacting with the above described anionic species, we typically mean a charge, measured as the Zeta potential, of at least 1 mV and preferably in the range of from 1 to 200 mV at pH 7.4 in 1 mM HEPES buffer. In order that the PEG-chitosan conjugate has sufficient positive charge, not more than 90% of the amine groups in chitosan should be PEGylated.

The person skilled in the art will be able to ascertain the degree of conversion necessary to meet the required pharmaceutical application.

The chitosans used for the preparation of the PEG-chitosan conjugates can have a molecular weight in the range of from 10 kD to 1000 kD, but more preferably will have a molecular weight in the range of from 10 kD to 500 kD, e.g., 20 kD to 500 kD, particularly from 30 kD to 300 kD, e.g., between 100 kD and 300 kD.

The degree of polymerization of the chitosans used in the preparation of the PEG-chitosan conjugates is typically in the range of from 50 to 6000, preferably in the range of from 100 to 3000 and particularly in the range of from 150 to 2000.

The polyethylene glycol content of the PEG-chitosan conjugate is typically from 1 to 50% on a weight basis, preferably from 5 to 20%.

Chitosans that have been derived by modification of the hydroxyl function could also be used. Such derivatives include O-acetylated and alkylated materials such as O-benzoyl chitosan and O-sulphated chitosans as detailed in Chitin Chemistry, A F Roberts, Macmillan, 1992, p. 166. Thus, in the present invention, the chitosan moiety in the PEG-chitosan conjugate may be a chitosan derivative and by the term chitosan we are also intending to include derivatives thereof. Preferably, however, the chitosan is unmodified.

The PEG-chitosan conjugate can be used to modify surfaces that are negatively charged or to interact with or form complexes with negatively charged molecules such as DNA, DNA plasmids or nucleic acids. The positively charged chitosan can bind strongly to such a negative surface and in doing so will expose the PEG group to the external environment. Such an exposed polyethylene glycol group will tend to provide for steric stabilization. This can lead to an improved stability, e.g., for a colloidal dispersion, but can also have important biological implications in minimizing the uptake of proteins to the surface of a particle, e.g., when the particle is injected into the bloodstream or administered to a body compartment.

The PEG-chitosan conjugate or adduct may be prepared using techniques known in the art for bonding PEG moieties to polymeric materials.

In one embodiment, the PEG-chitosan conjugate is prepared by a process comprising the steps of:

(1) preparing an activated PEG or an activated PEG derivative by incorporating an acrylic ester, an acrylic thioester or an acryloamido group into the PEG or PEG derivative;

(2) reacting the activated PEG or PEG derivative with chitosan; and (3) recovering the conjugate of the PEG or PEG derivative and chitosan.

This process allows the reaction between the PEG or PEG derivative and chitosan to be controlled.

By a PEG derivative we mean a modified polyethylene glycol, for example polyethylene glycol in which one or both of the terminal hydroxyl groups has been previously modified. Suitable PEG derivatives include alkoxy PEGs in which a terminal hydroxyl group(s) has been converted into an alkoxy group, i.e., a group having the formula RO— in which R is alkyl. Preferred PEG derivatives are those comprising a single alkoxy terminal group. Preferred alkoxy groups are $C_{1-4}$ alkoxy, such as methoxy.

The preparation of a PEG or PEG derivative carrying an acrylic ester group can be carried out by reacting a PEG or PEG derivative containing a hydroxyl function with acryloyl chloride.

The preparation of a PEG or PEG derivative carrying an acrylic thioester group can be carried out by reacting a PEG or PEG derivative containing a sulfhydryl group with acryloyl chloride. The preparation of a PEG or PEG derivative carrying an acrylamido group can performed by reacting PEG or PEG derivative containing one primary or secondary amine function with acryloyl chloride. The activated PEG or PEG derivative can be characterized by Gel Permeation Chromatography (GPC), FT-IR and UV spectroscopy. The degree of activation can be determined by end-group titration which involves adding an excess of 2-mercaptoethanol and titrating excess thiol with a calibrated $KI/I_2$ solution, or by UV spectroscopy, after calibration with a standard acrylamide or acrylic ester such as N-acryloylmorpholine or tetraethyleneglycol diacrylate, conducted at 233 nm.

Activated PEGs or activated PEG derivatives can be stored for several months at T≦4° C. in the presence of a desiccant. A radical inhibitor such as 4-methoxyphenol may also be added to prevent radical polymerization.

The reaction of the activated PEG or activated PEG derivative with chitosan is preferably preformed in an aqueous media. Alcohols or alcohol/water mixtures can also be used. The pH of reaction medium is preferably at least 8 and typically in the range of 8 to 9. The preferred reaction temperature is between 20 and 30° C. and typical reaction times are 12–48 hours. The occurrence of vinyl radical polymerization is inhibited by conducting the reaction under inert atmosphere, in the dark and in the presence of a radical inhibitor such as 4-methoxyphenol. The molecular weight of the PEG or the PEG portion in the case of a PEG derivative is typically between 1 and 30 kD, preferably between 2 and 20 kD and more preferably between 2 and 10 kD.

Recovery of the PEG-chitosan conjugate or adduct is generally carried out by ultrafiltration in water or by evaporating the reaction solvent and extracting the crude material with a new solvent.

The purity of the adduct can be assessed by GPC, FT-IR, NMR and UV spectroscopy. Checking for residual activated PEG or activated PEG derivative is usually performed spectrophotometrically at 233 nm.

The method can have advantages over other PEGylation processes known in the art because;

(a) free base is the species reacting with the double bond so that the reaction rate tends to increase with increase in pH, i.e., with increasing the concentration of free base;

(b) no by-product is produced during the reaction; and (c) the aminic character of the amino groups on the chitosan is not changed as a consequence of the grafting reaction.

In another embodiment, the PEG-chitosan conjugate is prepared by a process which involves activating the chitosan rather than the PEG or PEG derivative. Activation of the chitosan is preferably achieved by adding a large excess of a bis(acrylamide) to the chitosan. After the chitosan has reacted with the bis(acrylamide), the excess bis(acrylamide) is preferably removed and the activated chitosan reacted with a PEG or PEG derivative, preferably a monofunctional PEG carrying a hydroxyl, sulfhydryl or primary or secondary amino group.

Accordingly, in a further aspect of the present invention, there is provided a process for preparing a PEG-chitosan conjugate comprising the steps of:

(1) preparing an activated chitosan by reacting it with a bis(acrylamide);

(2) optionally removing any excess bis(acrylamide);

(3) reacting the activated chitosan with a PEG or PEG derivative, preferably a monofunctional PEG carrying a hydroxyl, sulfhydryl or primary or secondary amino group, and (4) recovering the conjugate of the monofunctional PEG and chitosan.

Grafting bis(acrylamide) to chitosan may make the chitosan more soluble or at least more swellable at pH>8 and, moreover, may provide for reactive functions which are more accessible than the original $NH_2$ groups which are close to the main polymer chain.

Furthermore, activating the chitosan with bis(acrylamide) may allow higher amounts of PEG to be grafted or bonded to the chitosan.

The PEG-chitosan conjugates prepared by the above described methods comprise a chitosan moiety and a PEG moiety which are joined together through a linking group or coupling moiety having the formula —$CH_2CH_2C(O)$—$R^2$—X—. The linking group is bonded to the amino nitrogen on the chitosan moiety via the —$CH_2CH_2$— group and to the PEG moiety via the X group. In the linking group, $R^2$ is a bond or a divalent organic group, X is oxygen, sulphur or —$NR^3$— and $R^3$ is H or an organic group such as alkyl, e.g., $C_{1-10}$ alkyl.

Accordingly, in a further aspect of the present invention, there is provided a PEG-chitosan conjugate having the formula:

wherein:

$C_m$ is the remainder of the monomeric unit making up the chitosan moiety or a derivative of such a monomeric unit;

p is an integer and represents the number of monomeric units of formula —$C_m$—$NR^1{}_2$— in the chitosan moiety, each $R^1$ is independently H or a group-A-PEG providing that at least proportion of the $R^1$ groups are -A-PEG;

each PEG is independently a polyethylene glycol moiety or a derivative thereof;

each A is independently a linking group having the formula —$CH_2CH_2$—C(O)—$R^2$—X— which is bonded to the amino nitrogen on the chitosan moiety via the —$CH_2CH_2$— group and to the PEG moiety via the X group;

$R^2$ is a bond or a divalent organic group;

X is oxygen, sulphur or —$NR^3$—; and $R^3$ is H or an organic group, or a physiologically acceptable derivative thereof.

For the avoidance of doubt, in referring to $C_m$. as the remainder of the monomeric unit making up the chitosan moiety we are referring to a group which together with the —$NH_2$— group makes up the full monomeric unit found in chitosan. Thus, the complete monomeric unit itself has the formula $C_m$—$NH_2$. By a derivative of such a monomeric unit we are referring to physiologically acceptable derivatives in which a hydroxyl group has been modified. Suitable derivatives include O-acetylated and alkylated materials such as O-benzoyl chitosan and O-sulphated chitosans as detailed in Chitin Chemistry, A F Roberts, MacMillan 1992, p. 166.

$C_m$ is preferably the remainder of the monomeric unit making up the chitosan.

p is preferably an integer in the range of from 50 to 6000, more preferably in the range of from 100 to 3000 and particularly in the range of from 150 to 2000.

PEG is preferably a modified polyethylene glycol moiety having the formula $R^4$—$(OCH_2CH_2)_n$— where $R^4$ is an aliphatic, alicyclic or aromatic hydrocarbon group, such as an alkyl, cycloalkyl, aryl or aralkyl group, and n is an integer. Preferably $R^4$ is alkyl, more preferably $C_{1-10}$ alkyl, e.g., $C_{1-4}$ alkyl, and especially methyl. n is suitably in the range of from 10 to 1000 and is preferably in the range of from 10 to 100.

$R^2$ is preferably a bond or a divalent organic group having the formula:

(II)

where $R^5$ is a divalent group which is bonded to the carbonyl (C(O)) group of linking group A. Preferably $R^5$ is bonded to the carbonyl group in Formula II above and the carbonyl group of linking group A via nitrogen atoms. More preferably, $R^5$ is a group having the formula:

(III)

(IV)

where each $R^6$ is independently a linear or branched $C_{1-4}$ alkyl chain, $R^7$ is a divalent organic group, particularly a linear or branched $C_{1-4}$ alkylene chain and $R^8$, $R^9$, $R^{10}$, and $R^{11}$ are each independently H or a linear or branched $C_{1-3}$ alkyl chain.

X is preferably oxygen or —$NR^3$—.

Suitable organic groups for $R^3$ include hydrocarbon groups such as alkyl, e.g. $C_{1-10}$ alkyl. Preferably $R^3$ is a hydrogen atom (H).

The structure of the PEG-chitosan conjugates resulting from the two methods described above is somewhat different. For example, if we employ an aminated monomethoxy-PEG having the structure:

(V)

and if chitosan is represented as:

(VI)

where represents the polymeric chain in chitosan and —$NH_2$ represents a single primary amine group in the chain, then the conjugate prepared by activating the aminated monomethoxy-PEG with an acrylamido group and reacting the activated compound with chitosan has the structure:

(VII)

In contrast, if the alternative process is employed in which the chitosan is activated by reacting it with a bis(acrylamide) having the structure:

(VIII)

where $R^5$ is a group having the formula:

(III)

(IV)

the corresponding conjugate has the following structure:

(IX)

wherein:
R is hydrogen or a second PEG chain bound to chitosan in the same way, that is through an acrylamide (method 1) or a bis(acrylamide) (method 2) coupling moiety;
$R^6$ is a linear or branched $C_{1-4}$ alkyl chain;
$R^7$ is a linear or branched $C_{1-4}$ alkylene chain; and
$R^8$, $R^9$, $R^{10}$, and $R^{11}$ are each independently H or a linear or branched $C_{1-3}$ alkyl chain.

In drug targeting and drug delivery, as well as in diagnostic imaging and in the administration of vaccine systems, particulate materials in the form of emulsions, liposomes, microparticles, microcapsules, and nanoparticules are employed. Such particles often carry a net negative charge. It is often important to be to modify this negative charge through the process of surface modification. For example, as mentioned above, the properties of liposomes can be modified by the adsorption of chitosan. It is now possible through the present invention to modify such particles with the PEG-chitosan system so that the particle carries not only a positive charge but a polyethylene glycol group that will provide for steric stabilization and beneficial biological and physical properties.

In the field of gene therapy, it is often important to be able to compact a plasmid material comprising nucleic acids into a small particle for improved administration. We have discovered that a PEG-chitosan conjugate can be used to compact plasmid DNA. The compacts produced should have enhanced solubility and beneficial properties for the interaction with cells and the subsequent expression of the gene product.

The PEG-chitosan material described herein could be further modified by the attachment of targeting ligands to the hydroxyl and unmodified amino functions in order to achieve site specific targeting. Such ligands can take the form of sugars and proteins. The latter can include monoclonal antibodies and fragments thereof. The sugars include mannose, fucose, and galactose. The choice of sugar will be dictated by the nature of the tissue or cell that is identified as the target site. For example, a complex of PEG-chitosan with DNA could be targeted to the liver by the covalent attachment of a triantennary galactose moiety.

The present invention is now illustrated but not limited with reference to the following examples.

EXAMPLE 1

Preparation of PEG-chitosan Using Activated PEG (A) Preparation of monomethoxy-PEG piperazinyl formate (MPEG-PF)

Monomethoxy-PEG 1900 (12.26 g, 6.45 mmol) was dissolved in "alcohol-free" $CHCl_3$ (60 ml). The solution was dried overnight over calcium hydride, which was then removed by filtration. 1,1'-carbonyldiimidazole of 97% purity (2.16 g, 12.9 mmol) was then added and the resulting solution allowed to stand at 30° C. for 30 minutes after which cold water was added (10 ml) and the mixture stirred for 10 minutes. After separation of the phases, anhydrous piperazine (0.56 g, 12.0 mmol) was added to the organic phase and allowed to react for 20 hours at 25° C. The solution was then diluted with $CHCl_3$ (100 ml), extracted with water (5×30 ml), dried with $Na_2SO_4$, filtered, concentrated in vacuo to 60 ml and finally poured into diethyl ether at about 10° C. The powder which precipitated out was collected by filtration and dried to constant weight at 0.1 torr. The yield was 10.64 g. The GPC chromatogram exhibited one peak with retention time 1030 sec. The FT-IR spectrum showed a band in the urethane region at 1703 $cm^{-1}$. The molecular weight, determined by potentiometric titration with 0.1 M HCl, was 2190.

(B) Preparation of monomethoxy-PEG acrylamide (MPEG-AA)

MPEG-PF (7.07 g; 3.23 mmol) was dissolved in dry, "alcohol-free" $CHCl_3$ (10 ml) and distilled water (2 ml) was added. 2.4 ml of a 2M solution of acryloyl chloride in $CHCl_3$ (4.8 mmol) and 2.4 ml of a 2M NaOH aqueous solution (4.8 mmol) were then added together, drop-wise, under vigorous stirring while maintaining the temperature at about 5° C. Once the addition was completed, the reaction mixture was left at 25° C. in the dark and under stirring for 1 hour. The reaction mixture was then diluted with $CHCl_3$ to 150 ml and washed in a separatory funnel with 5% $KNO_3$ (2×30 ml) and water (1×30 ml). After drying with $Na_2SO_4$ and filtering, the volume was reduced to about 50 ml by evaporating most of the $CHCl_3$ in vacuo. The solution was then diluted with diethyl ether (200 ml). The product which precipitated out was collected by filtration and dried to constant weight at 0.1 torr. The yield was 6.05 g. The GPS chromatogram exhibited one peak with retention time 1020 sec. The FT-IR spectrum was very similar to that of starting MPEG-PF, but showed an amidic band at 1649 $cm^{-1}$. The molecular weight, determined spectrophotometrically at 233 nm in water using the calibration curve of N-acryloylmorpholine, was 2300.

(C) PEGylation of chitosan

Chitosan hydrochloric salt (SeaCure CL 113) (1.03 g, 5.2 meq), MPEG-AA (3.91 g, 1.7 mmol) and 4-methoxyphenol (5 mg) were dissolved in distilled water and the pH of this mixture was raised to 8 by adding drop wise and under vigorous stirring triethylamine dissolved in a 3:1 $H_2O$/ $CH_3OH$ mixture. A precipitate was formed at pH>7. The reaction mixture was stirred at 25° C. under a nitrogen atmosphere and in the dark for 10 days. The pH was brought up to 3–4 by addition of diluted HCl and the resulting solution was freeze-dried. The powder was collected, extracted in a Soxhlet apparatus with a 3:1 diethyl ether/ $CH_2Cl_2$ mixture and dried in vacuo up to constant weight. The yield was 1.20 g.

The UV spectrum recorded in water did not exhibit any peak at 233 nm indicating that no residual MPEG-AA was present. In the FT-IR spectrum a shoulder at around 1700 $cm^{-1}$ was detected which was absent from the spectrum for native chitosan so indicating the presence of grafted PEG. Elemental analyses performed on the product (C: 37.69%, H:7.17%, N: 5.78%, CL: 14.09%), on starting chitosan (C: 34.91%, H: 6.42%, N: 6.56%, Cl: 17.04%) and on MPEG-AA (C: 54.49%, H: 8.87%, N: 1.25%) established that the PEG content was 14% by weight. Mohr titration of chloride ions executed on both the product and native chitosan confirmed this value.

The same process as described above has been used to prepare PEG-chitosan complexes from chitosans having molecular weight in the range 10,000 to 500,000 Daltons and from polyethylene glycol materials having molecular weights in the range 750 to 10,000 Daltons. The degree of conversion of the chitosan to the PEGylated form can be controlled through the chemical reaction.

In the above method for preparing the PEG-chitosan conjugate, it could be beneficial to increase the solubility of the chitosan at pH>7, and we have found that isobutyric acid gives a more soluble chitosan salt at about pH 7 compared to hydrochloric acid.

EXAMPLE 2

Preparation of PEG Chitosan Using Activated Chitosan (A) Preparation of monomethoxy-PEG piperazinyl formate (MPEG-PF)

Monomethoxy-PEG piperazinyl formate (MPEG-PF) was prepared using exactly the same technique as described in Example 1 (part A) above, but using monomethoxy-PEG 550 (3.55 g, 6.45 mmol) instead of monomethoxy-PEG 1900. The yield was 5.18 g.

(B) PEGylation of chitosan

Chitosan (Fluka; MW=70000) (0.40 g, 2.5 meq) was dissolved in distilled water (30 mls) containing isobutyric acid (0.22 g, 2.5 meq). 1,4-bis(acryloylpiperazine) (2.43 g, 12.5 mmol) was then added to the chitosan solution and allowed to react for 24 hours at 25° C. in the dark and under a nitrogen atmosphere. Unreacted 1,4-bis (acryloylpiperazine) was then removed by extraction with chloroform (8×5 ml). MPEG-PF was then added (3.25 g, 5.0 meq) to the aqueous phase and allowed to react for 10 days at 25° C. in the dark and under a nitrogen atmosphere, the pH being adjusted to 7 by the addition of isobutyric acid. The solution was freeze dried, extracted in the Soxhlet apparatus with a 3:1 diethyl ether/$CH_2Cl_2$ mixture and dried in vacuo to constant weight. The yield was 0.38 g.

Grafting of the PEG onto the chitosan was confirmed by FT-IR spectroscopy with a peak being observed at 1700 $cm^{-1}$ which is typical of PEG-piperazinyl formate and absent in native chitosan. From the ratio of the area of this peak to that at 1630 cm−1 (which is typical of chitosan), the PEG content was calculated to be around 20% by weight.

EXAMPLE 3

The Physical Adsorption of PEG-chitosan to Colloidal Particles

To illustrate the physical adsorption of PEG-chitosan to particles, polystyrene nanoparticles were used as a model system. The polystyrene particles were purchased from IDC Spheres, Interfacial Dynamics Corp., USA. The particles were stabilized with negative sulphate groups. The particle size of the unmodified lattices, as measured by photon correlation spectroscopy (PCS) (Malvern S4700, UK), was 190 nm.

Samples of the polystyrene particles were coated with either chitosan (SeaCure CL 113) or with a PEG-chitosan conjugate. The PEG-chitosan conjugate was prepared as in Example 1 from chitosan SeaCure CL 113obtained from Pronova Ltd., Norway. The chitosan had an average molecular weight of about 50 kD and an intrinsic viscosity of 153 ml/g. About 12% of the amino functions were acetylated (88% deacetylated). The average molecular weight of the attached PEG was 2100 and the degree of PEGylation 15%.

Different quantities of the chitosan and PEG-chitosan conjugate were added to 10 ml glass test tubes (0–100 μg) together with 1.5 ml of purified water. 0.5 ml of a 0.1% suspension of polystyrene particles was then added (representing 500 μg of particles) drop wise with vigorous stirring for 2 hours. The effect of the adsorbed chitosan and PEG-chitosan on the zeta potential of the particles was measured using a Malvern Zeta Sizer (Mark IV), Malvern Instruments, UK, at pH 7 4 in 1 mM HEPES buffer.

The uncoated polystyrene particles carried a net negative charge of –50 mV. The addition of chitosan or PEG-chitosan gave rise to a rapid charge reversal as measured using a Zeta Sizer so that the polystyrene particles carried a net positive charge of +20 mV upon the addition of 100 μg of chitosan or PEG-chitosan to 500 μg of the polystyrene particles suspended in 2 ml of an aqueous buffer solution. Hence both chitosan and PEG-chitosan have the ability to strongly adsorb to a negatively charged colloidal particle and reverse the charge. The point of zero charge was reached after the addition of 12 μg of chitosan to the system and 18 μg of PEG-chitosan to the system, demonstrating the difference between the PEGylated and unPEGylated materials. A similar difference could be seen for the addition of the same quantity of chitosan or PEG-chitosan to the system. For example, for 20 μg added cationic polymer the zeta potential was +13 mV for the chitosan system and +5 mV for the PEG-chitosan system.

The addition of a positively charged polymer to a negatively charged colloid such as polystyrene particles of 190 nm will give rise to flocculation. This process was investigated by measuring the optical density (OD) of the system at 600 nm after dilution 50:50 with the dispersion medium before measurement. For the addition of chitosan, the concentration of cationic polymer required to obtain a maximum OD of 0.66 was 5 μg (added to 500 μg of polystyrene particles in 4 ml). For the PEG-chitosan system, a maximum OD of 0.66 was obtained at 1.0 μg of PEG-chitosan added to 500 μg polystyrene particles suspended in 4 ml. Thus, both chitosan and PEG-chitosan cause flocculation of negatively charged model colloidal particles, but the quantities required were different so reflecting the difference between PEG-chitosan and chitosan.

The ability of coated particles to withstand flocculation was measured by studying the effect of added sodium sulphate ($Na_2SO_4$). The $Na_2SO_4$ induced flocculation of coated polystyrene particles (190 nm) was measured using a weight ratio of chitosan or PEC-chitosan to particles of 1:5. The optical density (OD) at 600 mm was used to assess the properties of the coated particles.

Figure 1:
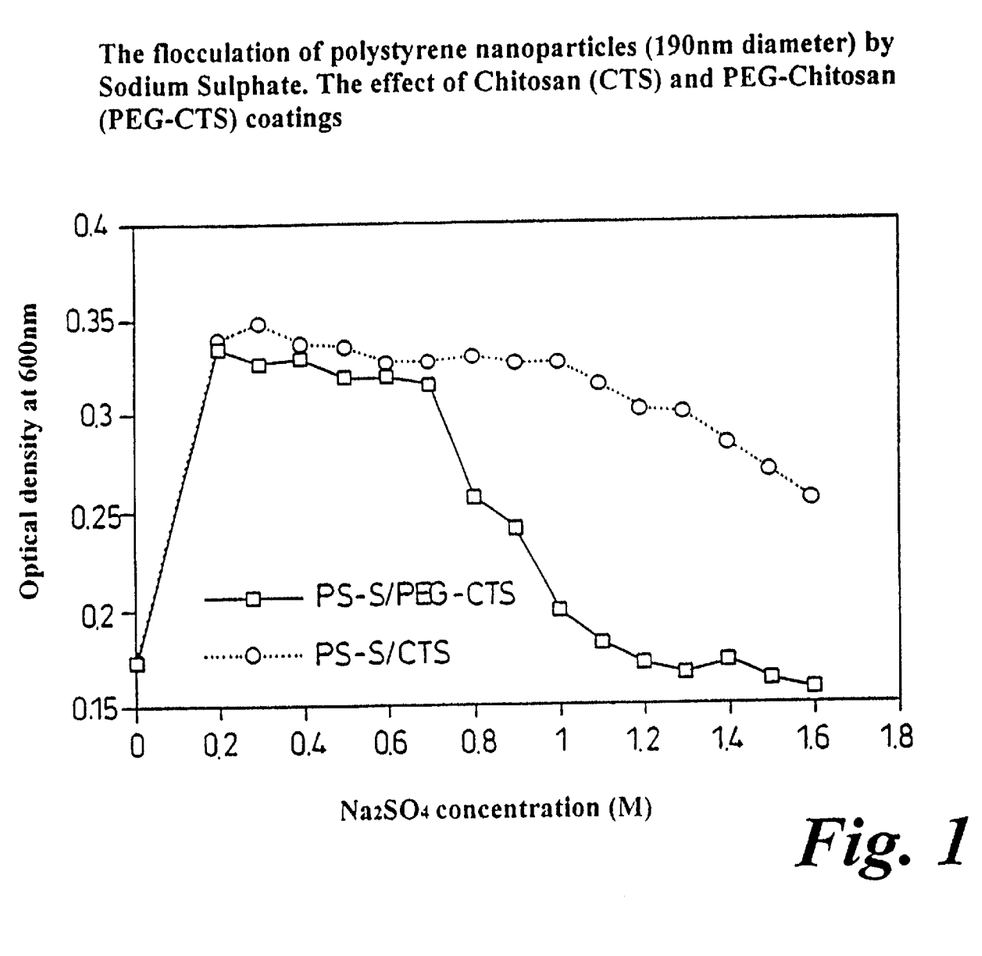
FIG. 1 is a graph showing the effect of added $Na_2SO_4$ on the properties of polystyrene particles (190 nm) coated with chitosan or PEG-chitosan.

FIG. 1 shows the effect of added $Na_2SO_4$ on the properties of polystyrene particles (190 nm) coated with chitosan and PEG-chitosan, respectively. (0.2 ml of polymer coated particles (10 μg chitosan or PEG-chitosan/50 μg polystyrene) in 0–1.6 M $Na_2SO_4$ solution). Both the chitosan and PEG-chitosan coated particles were affected by low concentrations of $Na_2SO_4$ (the uncoated particles required at least 0.25 M $Na_2SO_4$ to commence a change in OD). The OD of the chitosan coated particles remained constant at $Na_2SO_4$ concentrations above 0.8 M $Na_2SO_4$ while the PEG-chitosan coated particles demonstrated a change in OD).

The results again demonstrate the difference between chitosan and PEG-chitosan as coating materials.

EXAMPLE 4

Flocculation of Chitosan and PEG-Chitosan

The different properties of chitosan and PEG-chitosan can be measured by the $Na_2SO_4$ induced flocculation of solutions of the two cationic polymers. Two different quantities of the chitosan and PEG-chitosan as described in Example 3 were suspended in 0.4 ml of water, 0.1 mg and 1 mg. Then $Na_2SO_4$ was added to induce flocculation. The degree of flocculation was measured as previously as the OD at 600 nm. At an $Na_2SO_4$ concentration of 0.2 M the following OD figures were obtained.

| | |
|---|---|
| PEG-chitosan (0.1 mg) | OD = 0.005 |
| Chitosan (0.1 mg) | OD = 0.02 |
| PEG-chitosan (1 mg) | OD = 0.045 |
| Chitosan (1 mg) | OD = 0.13 |

The results show that for the same concentration of cationic polymer, the PEG-chitosan system is more stable to $Na_2SO_4$ induced flocculation than chitosan.

EXAMPLE 5

Compaction of DNA with PEG-Chitosan— Physiochemical Studies

In order to demonstrate the difference between the compaction of DNA with chitosan and the compaction of DNA with the PEG-chitosan conjugate, a model plasmid material was employed. This is in the form of the plasmid CMV-CAT that encodes for chloramphenicol acetyl transferase (CAT), a so-called reporter gene system. The p-CAT material was obtained from Gene Medicine, Inc., Houston, USA.

The interaction between a plasmid and a cationic polymer can be followed by a variety of techniques including the following:

(1) Particle size measurement on the complex using photon correlation spectroscopy.

(2) Measuring the zeta potential of the plasmid-complexing agent complex using particle microelectrophoresis.

(3) Measuring the state of compaction of the plasmid by studying the fluorescence of the plasmid DNA material in the presence of ethidium bromide.

(4) Titration microcalorimetry in which the heat of interaction between the positively charged polymer conjugate and the negatively charged DNA material is determined.

In this example and in Example 6 which follows, a number of the above techniques were used to illustrate the differences between compaction using chitosan and compaction with the PEG-chitosan system. The PEG-chitosan was prepared from a sample of SeaCure CL 113, where about 12% of the amino functions were acetylated. The method described in Example 1 was employed. The average molecular weight of the PEG bound to the chitosan was 2100. Unmodified chitosan SeaCure CL 113 was used as a control.

Photon Correlation Spectroscopy and Zeta Potential Measurements:

The pCAT-DNA/chitosan or the pCAT-DNA/PEG-chitosan complexes were prepared in the following way to give different pCAT-DNA/polymer ratios.

81.1 $\mu$g (100 $\mu$l) of pCAT-DNA in 2 ml of ultra pure water was slowly mixed with 525 $\mu$g of chitosan or PEG-chitosan (0.35 ml of a 0.15% solution) under stirring to give a pCAT-DNA:polymer weight ratio of 1:6.5.

81.1 $\mu$g (100 $\mu$l) of pCAT-DNA in 2 ml of ultra pure water was rapidly mixed with 810 $\mu$g of chitosan or PEG-chitosan (0.81 ml of a 0.1% solution) under stirring to give a pCAT-DNA:polymer weight ratio of 1:10.

The size of chitosan and PEG-chitosan complexes and their zeta potentials in water and 1 nM HEPES buffer at pH 7.4 were determined using a Malvern S4700 PCS and a Malvern Zeta Sizer (Mark IV), respectively. It can be seen from Table 1 that the surface properties of the chitosan-DNA complex are different from the properties of the DNA complex made with the conjugate that is the subject of the present invention. It is believed that the improved solubility of this complex and the difference in particle charge is beneficial for a biological response. Interestingly, the complexes formed by chitosan and PEG-chitosan with DNA produced small sized nanoparticles of about 140 nm as measured by PCS.

It will be appreciated by those skilled in the art that the size of the resulting complexes between plasmid DNA and a compacting polymer will be affected by the ratio of the interacting components and the processing conditions.

TABLE 1

Particle Size and Zeta Potential of Chitosan (PEG-chitosan)/DNA Complexes

| Ratio (w/w) | DNA/CTS | | DNA/PEG-CTS | |
|---|---|---|---|---|
| ($\mu$g/$\mu$g) | Size (nm) | ZP (mV) | Size (nm) | ZP (mV) |
| 1:6.5 | 138.3 | 32.2 | — | 20.9 |
| 1:10 | 172.5 | 40.4 | 140.8 | 31.2 |

EXAMPLE 6

In this example, a more detailed study of the interaction between selected plasmid DNA material (CMV-CAT) and PEG-chitosan was carried out. The plasmid was at a concentration of 1 mg/ml and the PEG-chitosan at 500 microgram/ml. The PEG-chitosan was centrifuged at 10,000 rpm for 10 minutes to remove any particulate from the solution. To a solution of 50 $\mu$g of DNA in 1 ml of water, was added an aliquot of PEG-chitosan solution equivalent to charge ratio DNA:PEG-chitosan of 1:0.25. The solution was stirred for 5 minutes and left to complex for 10 minutes.

The size of the complex was determined using Photon Correlation Spectroscopy. Further aliquots of PEG-chitosan were then added.

Figure 2:
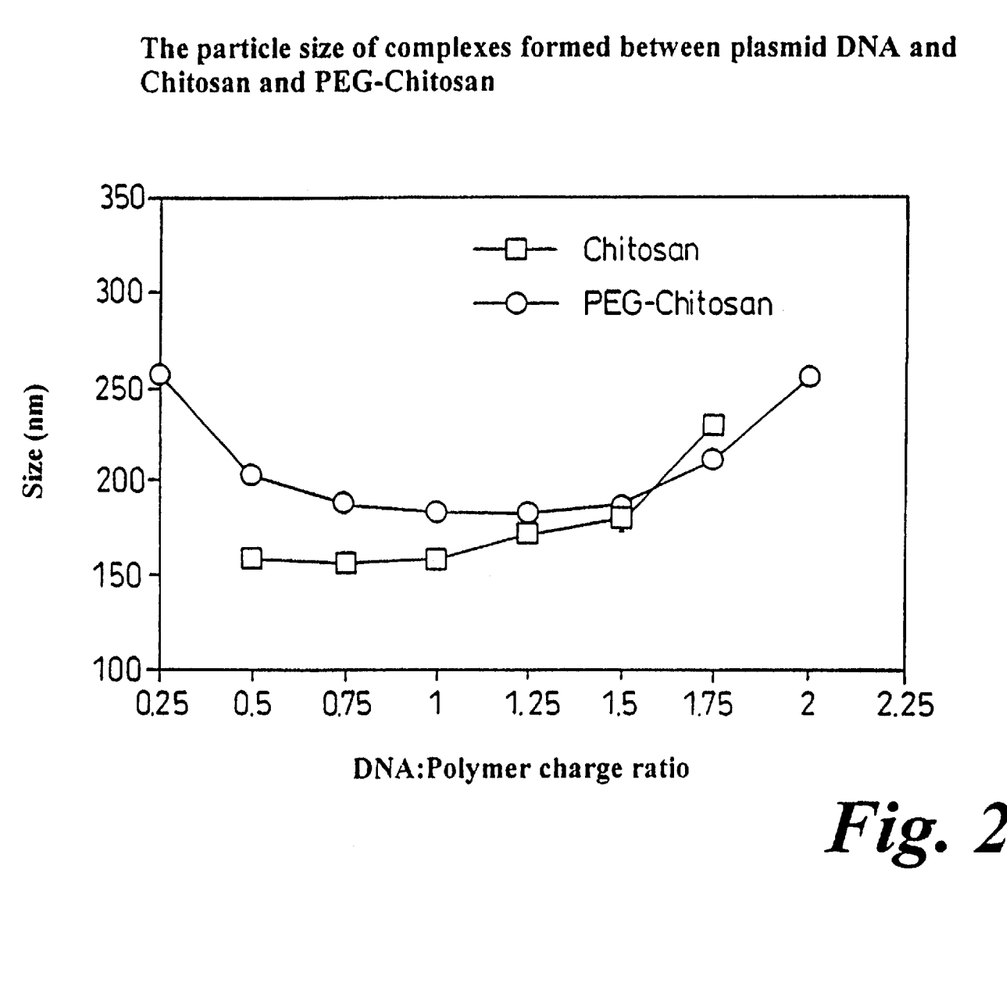
FIG. 2 is a graph showing the effect of increasing chitosan and PEG-chitosan concentrations on the size of the complexes formed between these materials and DNA.

FIG. 2 shows the effect of increasing chitosan and PEG-chitosan concentrations on the size of the resultant complexes. At low chitosan or PEG-chitosan concentration, there is not sufficient polymer to condense the plasmid DNA. However, at a ratio between 0.75–1.5 of DNA:PEG-chitosan or DNA-chitosan, a complex is formed which is reduced in size to less than 190 nm at a charge ratio close to 1:1. With further increase in polymer concentration, the size of complex increases. The results show the importance of the amount of PEG-chitosan added for complexing DNA with the polymer. The results also show that the presence of the PEG function does not greatly affect the condensing properties of chitosan. The greater size of the PEG chitosan complexes as compared to the chitosan complexes is considered to be due to the PEG group providing a steric barrier.

Fluorescence Study:

The interaction of DNA with chitosan and with the PEG-chitosan conjugate was examined through a process of fluorescence determination using ethidium bromide (EtBr) as a marker material. Plasmid DNA interacts (intercalates) strongly with the ethidium bromide to display strong fluorescence. However, if the plasmid is compacted then the fluorescence decreases markedly suggesting displacement.

The decrease in fluorescence was measured as follows.

8.11 $\mu$g of plasmid DNA was mixed with 2 $\mu$g of EtBr. The fluorescence of this complex was determined using a fluorescence spectrometer (Perkin-Elmer 3000, UK) with emission at 591 nm and excitation at 366 nm. 1 $\mu$g portions of chitosan or PEG-chitosan were added incrementally to the complex and the decreased fluorescence of the complex measured. Chitosan (CL 113) and PEG-chitosan were used to compare the efficiency of EtBr displacement.

Figure 3:
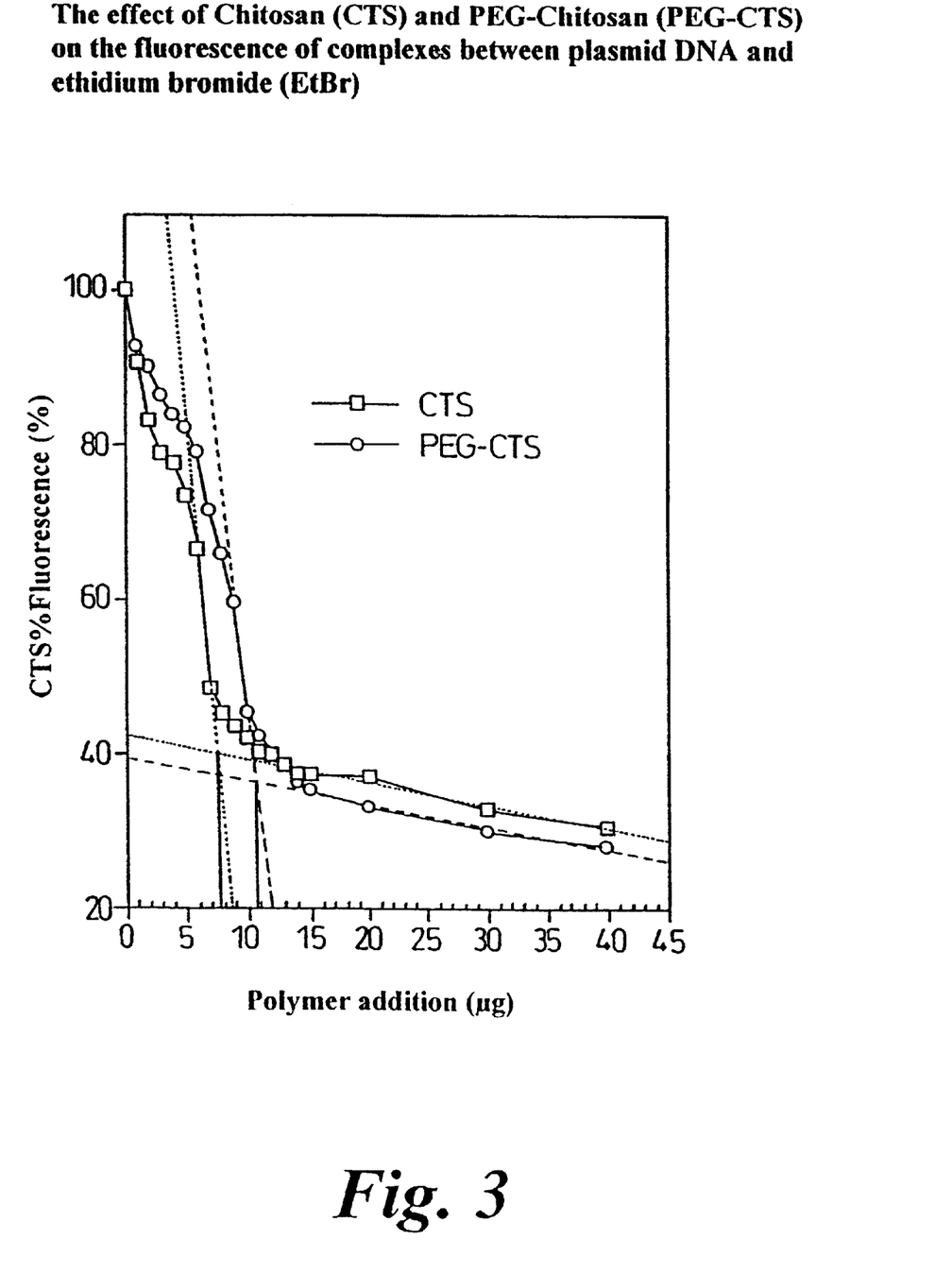
FIG. 3 is a graph showing the effect of adding chitosan and PEG-chitosan on the fluorescence of a DNA/ethidium bromide complex.

The displacement reaction is shown in FIG. 3. As seen in FIG. 3, the compaction of the selected plasmid DNA material with chitosan displays a different profile to the compaction with PEG-chitosan.

For chitosan (CTS) the displacement reaction finished when the addition of chitosan calculated from FIG. 3 was 7.47 $\mu$g. For PEG-chitosan (PEG-CTS) this value was 10.66 $\mu$g. At this point, the weight ratio of DNA:chitosan was 1:0.92 and the weight ratio of DNA:PEG-chitosan 1.31.

Although more PEG-chitosan was added to finish the displacement reaction on a weight basis, the molar concentrations of the two polymers were very close—0.033 $\mu$mol for chitosan and 0.039 $\mu$mol for PEG-chitosan.

The example shows that the PEGylation of chitosan does not substantially affect the ability of chitosan to interact strongly with plasmid DNA.

Microcalorimetry:

The interaction between chitosan and PEG-chitosan and a negatively charged plasmid was assessed by the heat exchange that occurred during the reaction using a technique known as isothermal titration microcalorimetry. A thermal activity monitor available from Thermometric, Model 2277 in Sweden was used to monitor the heat change.

The method involved injecting a solution of chitosan of PEG-chitosan from a precision syringe into two DNA solutions at specified time intervals. 2.0 ml of a DNA solution containing 81.1 $\mu$g pDNA was used for each experiment and 0.35 ml of the chitosan and PEG-chitosan solutions were added as 35 separate 10 $\mu$l injections. The time interval between two injections was about 10 minutes.

Each injection of chitosan or PEG-chitosan led to the evolution (exothermic process) or absorption (endothermic process) of heat which was picked up by the thermal activity monitor and recorded as a series of peaks, the value of which was calculated. The heat change was measured after each addition.

0.35 ml of the chitosan and PEG-chitosan solutions were also added to 2.0 ml distilled water as 35 separate 10 μl injections in order to determine the heat of dilution which was then subtracted from the measured heat exchange resulting from the interaction between chitosan and PEG-chitosan and the DNA solution.

Initially the interaction between the DNA and both the chitosan and PEG-chitosan was an exothermic process which became less exothermic as more of the chitosan and PEG-chitosan solutions were added, eventually becoming endothermic.

The interaction was followed by measuring the quantity of chitosan or PEG-chitosan needed to provide an endothermic response. The ratio of DNA to chitosan or PEG-chitosan at this point was then calculated (Table 2).

TABLE 2

The interaction between chitosan or PEG-chitosan and Plasmid DNA

| CTS or PEG-CTS | DNA/CTS or PEG-CTS ratio (w/w) |
|---|---|
| 0.05% CTS | 1:0.80 |
| 0.12% CTS | 1:0.74 |
| 0.15% CTS | 1:0.74 |
| 0.15% PEG-CTS | 1:1.11 |
| 0.20% PEG-CTS | 1:0.99 |
| 0.30% PEG-CTS | 1:1.11 |

The Stoichiometry of the Interaction can be Calculated:

The mean MW of plasmid DNA per phosphate group was calculated as 308.8 Daltons. The mean MW of chitosan (87% of deacetylation) per an amino group was calculated as 227.9 Daltons.

The mean MW of PEG-chitosan (15% of PEG 2100 w/w., 87% deacetylation) per an amino group was calculated as being 273.9 Daltons.

When the ratio of opposite charge units (or mole ratio) is 1:1, the ratio of DNA to chitosan by weight is 1:0.74 and DNA to PEG-chitosan by weight is 1:0.89. These theoretical values are very close to the experimental results obtained from the macrocalorimetry study. These results indicate that the PEG-chitosan can interact with DNA and form a complex.

The invention provides for the use of a PEG-chitosan material in drug delivery. The PEG moiety may confer advantageous properties, particularly in relation to the physiochemical properties of the chitosan material and the interaction of chitosan with surfaces, particles and DNA where it will be possible to provide a combination of positive charge (from those $NH_2$ groups of the chitosan that have not been PEGylated) and the PEG-modified amino groups. PEG-chitosan may also improve the paracellular transport of drugs as already described for chitosan itself. Moreover, the PEG-chitosan conjugate may be used to form controlled release materials in the form of microspheres, microparticles and matrices for administration to the gastrointestinal tract, to the vaginal cavity, to the nose and to the buccal cavity.

The conjugate could also be used for the administration of drugs to the eye wherein the chitosan would bind preferably to the mucus. Such an agent may also be used for the treatment of dry eye syndrome, where the PEG moiety provides a steric stabilization and lubricating effect. These products could be delivered to the eye using eye-drop systems known in the art.

PEG-chitosan complexes with carbohydrates such as alginates, xanthans, dextran sulphate and gellan could be beneficial as gels for drug delivery applications. PEG-chitosan can also be interacted with heparin and other negatively charged macromolecular drugs to form complexes. Nasal and vaginal products as liquids or powders based on PEG-chitosan can be delivered by conventional devices such as spray pumps, powder insufflators, or syringes.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A composition for the systemic uptake of a drug across a mucosal membrane comprising a polyethylene glycol-chitosan conjugate, wherein the polyethylene glycol-chitosan conjugate comprises a chitosan or chitosan derivative moiety and a polyethylene glycol or a polyethylene glycol derivative moiety, and the composition is formulated for delivery to a mucosal membrane.

2. The composition of claim 1, wherein the chitosan or chitosan derivative moiety has a molecular weight of 10 kD to 1000 kD.

3. The composition of claim 1, wherein the chitosan or chitosan derivative moiety has a molecular weight of 20 kD to 500 kD.

4. The composition of claim 1, wherein the chitosan or chitosan derivative moiety has a molecular weight of 100 kD to 300 kD.

5. The composition of claim 1, wherein the polyethylene glycol-chitosan conjugate is represented by the formula (I):

$$-[C_m-NR^1{}_2]_p- \quad (I)$$

wherein $C_m$ is a remainder of a monomeric unit of a chitosan or a chitosan derivative moiety;

p is an integer of 50 to 6000;

$R^1$ is independently selected from a hydrogen atom and wherein $R^2$ is selected from a bond and a first divalent organic group; X is selected from an oxygen atom, a sulphur atom, and the group $-NR^3-$, wherein $R^3$ is selected from a hydrogen atom and a monovalent organic group; and [PEG] is a polyethylene glycol or polyethylene glycol derivative moiety, provided that 1% to 99% of the groups represented by $R^1$ is 6. The composition of claim 5, wherein $C_m$ is the remainder of the monomeric unit making up chitosan.

7. The composition of claim 5, wherein p is an integer of 150 to 2,000.

8. The composition of claim 5, wherein [PEG] is $-R^4-(OCH_2CH_2)_n-$, and $R^4$ is a hydrocarbon group selected from the group consisting of an aliphatic hydrocarbon, an alicyclic hydrocarbon, and an aromatic hydrocarbon, and n is an integer of 10 to 1,000.

9. The composition of claim 8, wherein $R^4$ is an alkyl group.

10. The composition of claim 8, wherein $R_4$ is a methyl group.

11. The composition of claim 5, wherein $R^2$ is (II)

wherein $R^5$ is a divalent organic group that is bonded to the carbonyl group of $R^1$.

12. The composition of claim 5, wherein $R^2$ is and $R^6$ is independently selected from a linear or a branched alkyl group having one to four carbon atoms and $R^7$ is a divalent organic group.

13. The composition of claim 11, wherein $R^5$ is selected from the group consisting of (III)

wherein $R^6$ is independently selected from a linear or a branched alkyl group, and $R^7$ is a divalent organic group; and (IV)

wherein each of $R^8$, $R^9$, $R^{10}$, and $R^{11}$ is independently selected from a hydrogen atom and a linear or branched alkyl group having one to three carbon atoms.

14. A method for the preparation of a composition for the systemic uptake of a drug across a mucosal membrane comprising a polyethylene glycol-chitosan conjugate, the method comprising preparing the polyethylene glycol-chitosan conjugate by bonding the amino function of an activated chitosan species to a polyethylene glycol or polyethylene glycol derivative moiety.

15. The method of claim 14, wherein the activated chitosan species is prepared using bis(acrylamide).

* * * * *